United States Patent

White et al.

[11] 4,387,230
[45] Jun. 7, 1983

[54] PROCESS FOR PREPARING A DIHYDROPYRIDINE DERIVATIVE

[75] Inventors: Alan C. White, Windsor; Robin G. Shepherd, Burnham, both of England

[73] Assignee: John Wyeth and Brother Limited, Maidenhead, England

[21] Appl. No.: 294,678

[22] Filed: Aug. 20, 1981

Related U.S. Application Data

[63] Continuation of Ser. No. 183,790, Sep. 3, 1980, abandoned.

[30] Foreign Application Priority Data

Sep. 6, 1979 [GB] United Kingdom ............... 7930907

[51] Int. Cl.³ .................. C07D 211/02; C07D 211/86
[52] U.S. Cl. ..................................... 546/249; 546/296
[58] Field of Search .............................. 546/249, 296

[56] References Cited

U.S. PATENT DOCUMENTS

| | | | |
|---|---|---|---|
| 4,083,850 | 4/1978 | Koeda et al. | 546/296 |
| 4,216,218 | 8/1980 | Klioze et al. | 546/216 |
| 4,248,876 | 2/1981 | White | 546/216 |

Primary Examiner—Norma S. Milestone
Attorney, Agent, or Firm—George Tarnowski

[57] ABSTRACT

Dihydropyridines of formula

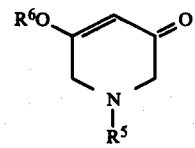

where $R^6$ is lower alkyl and $R^5$ is lower alkyl or aryl(lower)alkyl are prepared by a novel process from sodium or potassium salts of 1-substituted-1,6-dihydro-5-hydroxy-3[2H]-pyridones. The dihydropyridines are useful as intermediates for pharmacologically active 1-optionally substituted-3-phenyl or substituted phenyl-piperidin-5-ols and esters. Some of the piperidinols and esters are novel; those where the 1-substituent is aryl(lower)alkyl are intermediates, those where the 1-substituent is cycloalkyl(lower)alkyl are analgesics or antidepressants and those in which the 1-position is unsubstituted are anti-secretory agents.

1 Claim, No Drawings

PROCESS FOR PREPARING A DIHYDROPYRIDINE DERIVATIVE

This is a continuation of application Ser. No. 183,790 filed Sept. 3, 1980 now abandoned.

This invention relates to hereocyclic compounds. More particularly it relates to the preparation of dihydropyridine derivatives and their conversion to piperidine derivatives and to certain novel piperidine derivatives, to the use of such piperidine derivatives and compositions containing them.

The complete specification of our cognate U.K. patent application Nos. 681/77 and 48272/77 and the specification of the equivalent U.S. application, Ser. No. 866,311 now U.S. Pat. No. 4,248,876 (filed Jan. 3, 1978 in the name of Alan Chapman White under the title "Piperidine Derivatives") describe piperidine derivatives of general formula (I)

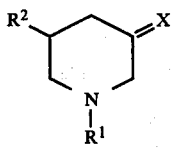
(I)

and the pharmaceutically acceptable acid addition salts thereof.

In general formula (I), $R^1$ represents (lower)alkyl, $R^2$ represents a phenyl group optionally substituted by one or more (lower)alkyl, (lower)alkoxy, halogen, amino, (lower)alkylamino, di(lower)alkylamino or trifluoromethyl substituents and X represents =O;

[where $R^3$ and $R^4$ both represent hydrogen, both represent the same (lower)alkyl or one is hydrogen and the other is (lower)alkyl or $R^3$ and $R^4$ together represent an alkylene group such that the

is a cyclic ketal group containing 2 or 3 carbon atoms]; or

[where OR is hydroxy, etherified hydroxy or esterified hydroxy].

We have now found a novel method for preparing the piperidine derivatives of general formula (I) and other related piperidine derivatives and their pharmaceutically acceptable acid addition salts. An important intermediate in the novel method is a dihydropyridine derivative of general formula (II)

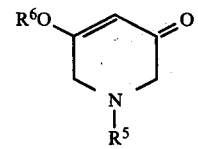
(II)

wherein $R^5$ is (lower)alkyl or aryl(lower)alkyl and $R^6$ is lower alkyl.

According to one aspect of the present invention there is provided a process for preparing a compound of general formula (II) which comprises alkylating an alkali metal salt of general formula (III)

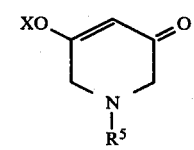
(III)

where $R^5$ is as defined above and X is sodium or, preferably, potassium. According to a preferred aspect of the invention the alkali metal salt of general formula (III) may be prepared by a process which comprises cyclising an ester of general formula (IV)

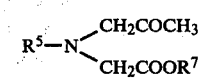
(IV)

(where $R^5$ is as defined above and $R^7$ is alkyl, aryl, e.g. phenyl, or aralkyl, e.g. benzyl) with sodium or potassium hydride. Preferably $R^7$ is lower alkyl. The cyclisation may be carried out in an inert organic solvent and the alkali metal salt of general formula (III) isolated. The cyclisation of compound (IV) and the isolation of the alkali metal salt of formula (III) followed by its subsequent alkylation enables the dihydropyridine derivative to be prepared in good overall yield compared to the yields given in Tamura et al, Tetrahedron Letters, 1977, 4075–4078 and Ziegler et al, J. Amer. Chem. Soc., 1973, 95, 7458–7464. The starting compounds of formula (IV) may be prepared by the method described in the above mentioned references.

The alkali metal salt of general formula (III) may be alkylated to the dihydropyridine of general formula (II) by treatment with an alkylating agent in a polar aprotic solvent, e.g. hexamethylphosphoric triamide, dimethylformamide, dimethylsulfoxide, or sulpholane. The alkylating agent is preferably an alkyl tolylsulphonate (e.g. methyl tolylsulphonate or n-hexyltolylsulphonate), an alkane sulphonate (such as methane sulphonate), a dialkyl sulphate such as dimethyl sulphate or an alkyl halide, (preferably an alkyl chloride).

The dihydropyridine derivatives of general formula (II) may be treated with an aryl lithium of formula $R^2Li$ or with a Grignard reagent of general formula $R^2MgY$ (where $R^2$ is as defined above and Y is a halogen atom), followed by acidic hydrolysis to give a dihydropyridine derivative of general formula (V)

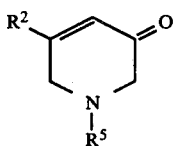 (V)

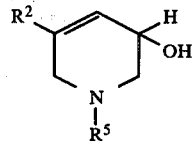 (VIII)

where R² and R⁵ are as defined above, or an acid addition salt thereof.

Compounds of general formula (V) and acid addition salts thereof can be converted to piperidine compounds of general formula (I) and related piperidine derivatives by, for example, the procedures described in the above mentioned specifications. For example, piperidine derivatives of general formula (VI)

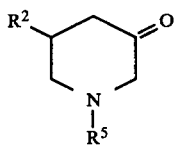 (VI)

where R² and R⁵ have the meanings given above, or pharmaceutically acceptable acid addition salts thereof may be prepared by reduction of the compound of general formula (V) or an acid addition salt thereof and, if desired, converting a free base of general formula (VI) into a pharmaceutically acceptable acid addition salt thereof.

The reduction of compounds of general formula (V) or acid addition salts thereof may be effected, for example, by catalytic hydrogenation. Suitable hydrogenation catalysts include, for example, palladium (particularly palladium on charcoal), platinum or nickel. Compounds of general formula (V) or acid addition salts thereof may also be reduced by alkali metal (e.g. lithium or sodium) in liquid ammonia.

Piperidine derivatives of general formula (VII)

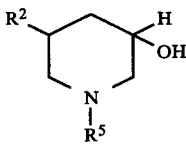 (VII)

where R² and R⁵ have the meanings given above, and pharmaceutically acceptable salts thereof may be prepared by reducing a compound of general formula (VI) or a pharmaceutically acceptable acid addition salt thereof with a carbonyl reducing agent.

The carbonyl reducing agent may be, for example, a hydride transfer reagent (e.g. sodium borohydride, lithium aluminium hydride, lithium tri-sec-butyl borohydride) or a catalytic reducing agent (hydrogen in the presence of a catalyst such as palladium charcoal or Raney nickel).

Compounds of formula (VII) may be prepared by an alternative process which comprises reducing a compound of general formula (VIII)

or an acid addition salt thereof, where R² and R⁵ have the meanings given above. The compound of formula (VIII) may, for example, be reduced by catalytic hydrogenation. The compound of general formula (VIII) may be prepared by reducing the compound of general formula (V) with, for example, a hydride transfer reagent (e.g. sodium borohydride).

When R⁵ in the compound of general formula (VII) is benzyl or a substituted benzyl such as alkyl- or alkoxybenzyl this may be removed by, for example, catalytic hydrogenation to give a compound of general formula (X)

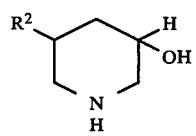 (X)

or a pharmaceutically acceptable acid addition salt thereof. The compounds of general formula (X) are particularly important intermediates since they can be alkylated to give compounds having the formula (VII) given above in which R² is as defined above and in which R⁵ is lower alkyl or R⁵ is cycloalkyl(lower)alkyl, e.g. cyclopropyl methyl and cyclobutyl methyl. In a preferred method of alkylation the compound of general formula (X) is treated with an acyl halide (e.g. a lower alkanoyl halide such as acetyl chloride or a cycloalkane carboxylic acid halide such as cyclopropane carboxylic acid chloride) and the resulting N-alkanoyl-3-acyloxy-piperidine compound reduced (e.g. with a hydride transfer reagent). In an alternative method of alkylation the compound of formula (X) is treated with an aldehyde and a reducing agent such as sodium cyanoborohydride. The compound of formula (X) can also be alkylated with an alkyl halide in presence of an acid acceptor.

The esters of the compounds of general formula (VII) and (X) may be prepared by esterifying the corresponding free alcohol or its acid addition salt.

If in any of the processes described above the compound of the invention is obtained as an acid addition salt, the free base can be obtained by basifying a solution of the acid addition salt although, as mentioned above, if the product of any of the processes is a free base, a pharmaceutically acceptable acid addition salt may be obtained by dissolving the free base in a suitable organic solvent and treating the solution with an acid, in accordance with conventional procedures for preparing acid addition salts from base compounds. Examples of acid addition salts are those formed from inorganic and organic acids such as sulphuric, hydrochloric, hydrobromic, phosphoric, tartaric, fumaric, maleic, citric, acetic, formic, methanesulphonic and p-toluenesulphonic acids.

The piperidine compounds prepared according to the invention possess at least one asymmetric carbon atom and hence the compounds may be, for example, in the form of optically active enantiomers or as mixtures of such enantiomers, e.g. racemates. The optical isomers may be prepared by various processes. For example, a racemic mixture may be resolved by standard methods described in the literature such as by use of an optically active acid. An optical isomer may also be prepared by using an asymmetric reduction method.

The piperidine alcohols (e.g. of formulae VII and X) and their esters possess two asymmetric carbon atoms and hence the compounds can exist in various stereochemical forms all of which are provided by the invention. The proportions of the cis and trans isomers in the alcohol depend on the reducing agent used in its method of preparation.

The term "lower" as used herein to qualify a radical means that the radical contains from 1 to 6, preferably from 1 to 4 carbon atoms. For example when $R^5$ is a (lower)alkyl group it is preferably methyl, ethyl, propyl or butyl. When $R^5$ is aryl(lower)alkyl the radical is preferably a phenyl(lower)alkyl group such as phenethyl or more particularly benzyl; the phenyl group may be substituted by, for example, one or more substituents such as halogen, alkoxy, trifluoromethyl or other substituents common in medicinal chemistry. $R^2$ can be an unsubstituted phenyl group or a phenyl group substituted by one or more (lower)alkyl (such as methyl, ethyl, propyl or butyl), hydroxy, (lower)alkoxy (such as methoxy, ethoxy, propoxy or butoxy), halogen (e.g. chlorine or fluorine), amino, lower(alkyl)amino (e.g. methylamino), di(lower)alkylamino (e.g. dimethylamino) or trifloromethyl groups.

Certain of the above mentioned piperidine derivatives are novel and the present invention, in a further aspect provides:

(a) Compounds of general formula (VI), and their pharmaceutically acceptable acid addition salts in which $R^2$ has the meaning given above and $R^5$ is aryl(lower)alkyl. These compounds are useful as intermediates for preparing other piperidine derivatives as described above.

(b) Alcohols of general formula (VII), and their pharmaceutically acceptable acid salts, wherein $R^2$ is as defined above and $R^5$ is aryl(lower)alkyl or cycloalkyl(lower)alkyl, and the corresponding esters. These compounds possess pharmacological activity or are useful as intermediates for other alcohols of general formula (VII) as described above. Compounds in which $R^5$ is cycloalkyl(lower)alkyl are particularly useful because they possess analgesic and antidepressant activity, as indicated by tasting in standard pharmacological test procedures. For example, a representative compound, cis-1-cyclopropylmethyl-3-hydroxy-5-phenylpiperidine, produced analgesia in 8 our of 10 rats at a intraperitoneal dose of 25 mg/kg when tested by a rat tail flick method for analgesic activity based upon D'Amour and Smith, J. Pharmacol., 1941, 72, 74. An example of a test for antidepressant activity is one based upon that of B. M. Askew, Life Sciences (1963), 1, 725–730.

(c) Alcohols of general formula (X) wherein $R^2$ is as defined above, and their pharmaceutically acceptable acid addition salts, and the corresponding esters. These compounds are intermediates for preparing N-substituted piperidine derivatives as described above. In addition the compounds possess pharmacological activity, in particular the compounds are anti-ulcer agents which possess anti-secretory activity in the standard test of H. Shay et al Gastroenterology, 1954, 26, 906–913.

The invention further provides a pharmaceutical composition which comprises an alcohol of general formula (VIII) wherein $R^2$ is as defined above and $R^5$ is cycloalkyl(lower)alkyl or of general formula (X) wherein $R^2$ is as defined above or a corresponding ester or a pharmaceutically acceptable acid addition salt thereof, in association with a pharmaceutically acceptable carrier. The active ingredients of the compositions should, of course, be chosen so that they are stable in the particular composition employed. In the compositions of the invention the carrier may be a solid, liquid or mixture of a solid and liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders are tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting was and cocoa butter. The term "composition" is intended to include the formulation of an active ingredient with encapsulating material as carrier to give a capsule in which the active ingredient (with or without other carriers) is surrounded by carrier, which is thus in association with it. Similarly cachats are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol containing from 10 to 75% of the glycol by weight is generally suitable.

In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from about 5 mg. to 500 mg., according to the particular need and the activity of the active ingredient. The invention also includes the compounds in the absence of carrier where the compounds are in unit dosage form. The daily dose of compound will vary depending upon the route of administration, the particular compound employed and the particular animal involved.

The following Examples illustrate the invention.

EXAMPLE 1

1-Benzyl-1,6-dihydro-5-methoxy-3[2H]-pyridone (a) A suspension of potassium hydride (90 g of 24% dispersion in oil) in ether (2.5 l) was treated with t-butanol (2.5 ml) followed by a solution of ethyl N-acetonyl-N-benzylglycinate (125 g) in ether (125 ml). The reaction mixture was stirred 1 hour and the resultant precipitate removed by filtration, washed with ether and dried in vacuo to give the potassium salt of 1-benzyl-1,6-dihydro-5-hydroxy-3[2H]-pyridone (125 g).

(b) A solution of the above potassium salt (125 g) in hexamethylphosphoric triamide (500 ml) was treated with methyl tosylate (93 g), the reaction mixture stirred 2 hours and then poured onto water (2.5 l). The resultant precipitate was removed by filtration, washed with water and air-dried. Recrystallisation from cyclohexane gave the title compound (60 g) m.p. 113°–115°.

Analysis: Found: C, 72.0; H, 7.2; N, 6.1%, $C_{13}H_{15}NO_2$ requires C, 71.9; H, 7.0; N, 6.5%.

EXAMPLE 2

1-Benzyl-1,6-dihydro-5-phenyl-3[2H]-pyridone

A solution of phenylmagnesium bromide (0.17 M) in ether (100 ml) was treated dropwise with a solution of 1-benzyl-1,6-dihydro-5-methoxy-3-[2H]pyridone (32.5 g, 0.15 M) in THF (150 ml), the reaction mixture stirred 1 hour and then poured onto cold 2 N hydrochloric acid (200 ml) and stirred 30 min. Removal of the resulting precipitate by filtration followed by air-drying and recrystallisation from methanol gave the title compound as the hydrochloride hydrate (32 g), m.p. 164°–6°.

Analysis: Found: C, 67.9; H, 5.9; H, 4.3%, $C_{18}H_{17}NO.HCl.H_2O$ requires C, 68.0; H, 6.3; N, 4.4%.

EXAMPLE 3 cis-1-Benzyl-3-hydroxy-5-phenylpiperidine

A solution of 1-benzyl-1,6-dihydro-5-phenyl-3-[2H]pyridone hydrochloride hydrate (25 g) in 50% aqueous methanol (500 ml) was treated with sodium bicarbonate (6.9 g) followed by sodium borohydride (6 g) in portions over 2 hours. The solvents were removed under reduced pressure and the residue partitioned between water (250 ml) and ether (250 ml). The organic phase was dried and the solvent removed under reduced pressure to yield an oil.

A solution of the above oil in ethanol (200 ml) was hydrogenated over 10% Pd/charcoal at atmosphere and room temperature. After the theoretical uptake of hydrogen had occurred (c. 3 h) the catalyst was removed by filtration and the solvent removed under reduced pressure. The resulting oil was dissolved in ether (500 ml) and treated with an excess of a solution of hydrogen chloride in ether. Removal of the resulting precipitate by filtration and recrystallisation from IPA gave the title compound as the hydrochloride quarter hydrate (18 g) m.p. 231°–4°.

Analysis: Found: C, 70.4; H, 7.6; N, 4.4%, $C_{18}H_{21}NO.HCl.\frac{1}{4}H_2O$ requires C, 70.1; H, 7.5; N, 4.5%.

EXAMPLE 4 cis-3-Hydroxy-5-phenylpiperidine

A solution of cis-1-benzyl-3-hydroxy-5-phenylpiperidine hydrochloride (6.16 g) in methanol (100 ml) was hydrogenated over 10% Pd/charcoal in a Parr apparatus at 50 psi (about $3.5 \times 10^4$ kg/sq.m.) and room temperature. After the theoretical uptake of hydrogen had occurred (about 7 hours) the catalyst was removed by filtration and the solvent evaporated under reduced pressure. Recrystallisation of the residue from IPA gave the title compound as the hydrochloride (3.1 g) m.p. 200°–4° C.

Analysis: Found: C, 61.85; H, 7.9; N, 6.3%. $C_{11}H_{15}NO.HCl$ requires: C, 61.8; H, 7.6; N, 6.6%.

EXAMPLE 5 cis-1-Cyclopropylmethyl-3-hydroxy-5-phenylpiperidine

A solution of cis-3-hydroxy-5-phenylpiperidine hydrochloride (3.6 g) in dichloromethane (50 ml) was treated with cyclopropane carboxylic acid chloride (10 ml) followed by triethylamine (10 ml). After 24 hours the reaction mixture was partitioned between water (200 ml) and methylene chloride (100 ml). The organic phase was washed with 2 N HCl, 2 N NaOH and water, dried and the solvents removed under reduced pressure. The residue was dissolved in THF (25 ml) and added to a solution of lithium aluminium hydride (1.3 g) in THF (25 ml). After 24 hours a saturated solution of Rochelle salt (50 ml) was added and the layers separated. The aqueous layer was extracted with chloroform (2×100 ml). The combined organic layers were washed with brine, dried and the solvents removed under reduced pressure. The residue was dissolved in ether (100 ml), filtered and treated with an excess of an ethereal solution of hydrogen chloride. Removal of the resultant precipitate by filtration, followed by recrystallisation from IPA gave the title compound as the hydrochloride (1.2 g) m.p. 194°–5°.

Analysis: Found: C, 66.8, H, 8.6; N, 4.7%, $C_{15}H_{21}NO.HCl$ requires C, 67.3; H, 8.3; N, 5.2%.

EXAMPLE 6 cis 1-Ethyl-3-hydroxy-5-phenylpiperidine (a) A solution of cis-3-hydroxy-5-phenyl-piperidine hydrochloride (3.6 g) in a mixture of dichloromethane (50 ml) and acetyl chloride (5 ml) was treated with triethylamine (10 ml). After 24 hours the reaction mixture was partitioned between water (200 ml) and dichloromethane (100 ml). The organic phase was washed with 2 N HCl, 2 N NaOH and water, dried and the solvents removed under reduced pressure. The residue was dissolved in THF (25 ml) and added to a solution of lithium aluminium hydride (1.3 g) in THF (25 ml). After 24 hours a saturated solution of Rochelle salt (50 ml) was added and the layers separated. The aqueous layer was extracted with chloroform (2×100 ml) and the combined extracts washed with brine, dried and the solvents removed under reduced pressure. Chromatography of the residue on Grade III silica, using 3% methanol in chloroform as eluant, evaporation of the appropriate fractions, conversion to the hydrochloride and recrystallisation from IPA gave the title compound as the hydrochloride (1.0 g) m.p. 182°–4°.

Analysis: Found: C, 64.3; H, 8.15; N, 5.9%, $C_{13}H_{19}NO.HCl$ requires C, 64.6; H, 8.3; N, 5.8%.

(b) 5-Phenyl-3-piperidinol (5.2 g), tetramethylpiperidine (8.3 ml) and iodoethane (1.97 ml) was stirred at room temperature in methanol (100 ml) for 48 hours. The methanol was removed under reduced pressure and excess 2 M NaOH added. The oil was extracted with ether and washed with brine. After drying ($MgSO_4$) the ether was removed and the product crystallised affording, after recrystallisation from cyclohexane, 3.2 g of pure title compound which could be converted to the hydrochloride salt m.p. 182°–4° C.

EXAMPLE 7

1-Benzyl-1,6-dihydro-5-(p-trifluoromethylphenyl)-3[2H]pyridone

A solution of p-trifluoromethylphenyl magnesium bromide (85 mM) in ether (50 ml) was treated dropwise with a solution of 1-benzyl-1,6-dihydro-5-methoxy-3-[2H]pyridone (16.3 g, 75 mM) in THF (75 ml), the reaction mixture stirred 1 hour, poured onto cold 2 N hydrochloric acid (150 ml) and stirred 30 min. Removal of the resultant precipitate by filtration, followed by air drying and recrystallisation from 95% ethanol gave the title compound as the hydrochloride hydrate, (15 g).

Analysis: Found: C, 58.9; H, 4.6; N, 3.5%, $C_{19}H_{16}F_3NO.HCl.H_2O$ requires C, 59.1; H, 5.0; N, 3.6%.

This material softens about 100°, solidifies about 125° and finally remelts 230°–3°.

EXAMPLE 8

1-Benzyl-5-hydroxy-1,2,5,6-tetrahydro-3-(p-trifluoromethylphenyl)pyridine

A solution of 1-benzyl-1,6-dihydro-5-(p-trifluoromethylphenyl)-3-(2H)pyridone hydrochloride hydrate (11.6 g) in ethanol (250 ml) was treated with sodium bicarbonate (2 g) followed by sodium borohydride (1.5 g). After 2 hours the solvents were removed under reduced pressure and the residue partitioned between water (100 ml) and ether (400 ml). The organic phase was dried and the solvent removed under reduced pressure. Recrystallisation of the residue from cyclohexane gave the title compound (7.3 g), m.p. 88°–90°.

Analysis: Found: C, 68.05; H, 5.3; N, 3.95%, $C_{19}H_{18}F_3NO$ requires C, 68.1; H, 5.5; N, 4.2%.

EXAMPLE 9 cis-3-Hydroxy-5-(p-trifluoromethylphenyl)piperidine

A solution of 1-benzyl-5-hydroxy-1,2,5,6-tetrahydro-3-(p-trifluoromethylphenyl)pyridine (5.9 g) in methanol (200 ml) was hydrogenated over 10% palladium on carbon (500 mg) in a Parr apparatus at 30 psi (about $2.11 \times 10^4$ kg/sq.m.) and room temperature. After the theoretical uptake of hydrogen had occurred (about 3 hours), the catalyst was removed by filtration and the solvent evaporated under reduced pressure. Recrystallisation of the residue from toluene gave the title compound as the free base (4 g). The free base was dissolved in a small volume of IPA and treated with an excess of etherial hydrogen chloride. On cooling crystals of the title compound hydrochloride separated, m.p. 189°–92°.

Analysis: Found: C, 51.0; H, 5.7; N, 4.7%. $C_{12}H_{14}F_3NO.HCl$. requires C, 51.2; H, 5.4; N, 5.0%.

EXAMPLE 10 cis-3-Hydroxy-1-methyl-5-(p-trifluoromethylphenyl)-piperidine

A solution of cis-3-hydroxy-5-(p-trifluoromethylphenyl)piperidine (2.1 g) in a mixture of acetonitrile (25 ml) and 40% aqueous formaldehyde (3.5 ml) was treated with sodium cyanoborohydride (900 mg). After 15 min. acetic acid was added to adjust the mixture to pH6 to 7. The pH was maintained in this range by further additions of acetic acid over 45 min. and the solvents removed under reduced pressure. The residue was partitioned between 2 N aqueous sodium hydroxide (20 ml) and ether (50 ml). The ether layer was extracted with 2 N hydrochloric acid (20 ml), the acid solution basified to pH9 with sodium carbonate and extracted with ether (2×50 ml). The organic phase was dried and the solvent removed under reduced pressure to give an oil which was converted to the hydrochloride and recrystallised from isopropanol/ether to give the title compound as the hydrochloride (1.2 g), sublimes 210°.

Analysis: Found: C, 52.5; H, 5.9; N, 4.6%, $C_{13}H_{16}F_3NO.HCl$ requires C, 52.8; H, 5.8; N, 4.7%.

EXAMPLE 11

1-Benzyl-1,6-dihydro-5-(p-tolyl)-3[2H]-pyridone

A solution of p-tolyl phenylmagnesium bromide (85 mM) in ether (50 ml) was treated dropwise with a solution of 1-benzyl-1,6-dihydro-5-methoxy-3-[2H]pyridone (16.3 g) in THF (75 ml), stirred 1 hour, the reaction mixture poured onto cold 2 N hydrochloric acid (150 ml) and stirred 30 min. The resulting precipitate was air dried and recrystallised from 95% ethanol to give the title compound as the hydrochloride hydrate (13 g) m.p. 169°–72°.

Analysis: Found: C, 68.7; H, 6.3; N, 3.9%. $C_{19}H_{19}NO.HCl.H_2O$ requires C, 68.8; H, 6.7; N, 4.2%.

EXAMPLE 12

1-Benzyl-5-hydroxy-1,2,5,6-tetrahydro-3-(p-tolyl)pyridine

A solution of 1-benzyl-1,6-dihydro-5-(p-tolyl)-3-[2H]-pyridone hydrochloride hydrate (4.7 g) in ethanol (100 ml) was treated with sodium bicarbonate (1.2 g), followed by sodium borohydridge (1 g). After 1 hour the solvents were removed under reduced pressure and the residue partitioned between water (50 ml) and ether (200 ml). The ether layer was dried and the solvent removed under reduced pressure to give the title compound as an oil (3.5 g).

EXAMPLE 13 cis-1-Benzyl-3-hydroxy-5-(p-tolyl)piperidine and cis-3-Hydroxy-5-(p-tolyl)piperidine A solution of the crude product of Example 12 (3.5 g) in ethanol (100 ml) was hydrogenated over 10% palladium on carbon (500 mg) at atmospheric pressure and room temperature. Uptake ceased after 0.6 molar equivalents of hydrogen had been consumed, hence further catalyst (500 mg) was added. Uptake ceased again after the consumption of 1.5 molar equivalents of hydrogen. The catalyst was removed by filtration, the filtrate treated with an excess of ethereal hydrogen chloride and the solvents removed under reduced pressure. Fractional crystallisation of the residue from isopropanol/ether gave cis-1-benzyl-3-hydroxy-5-(p- tolyl)piperidine hydrochloride quarter hydrate (500 mg) m.p. 238°–242°.

Analysis: Found: C, 70.6; H, 7.8; N, 4.1%, $C_{19}H_{23}NO.HCl1/4H_2O$ requires C, 70.8; H, 7.7; N, 4.3%, and cis-3-hydroxy-5-(p-tolyl)piperidine hydrochloride three quarters hydrate (900 mg) m.p. 200°–211°.

Analysis: Found: C, 59.95; H, 8.0; N, 5.4%, $C_{12}H_{17}NO.HCl.1/4H_2O$ requires C, 59.8; H, 8.1; N, 5.8%.

EXAMPLE 14

1-Benzyl-1,6-dihydro-5-(m-chlorophenyl)-3[2H]-pyridone

A solution of m-chlorophenyl magnesium bromide (85 mM) in ether (50 ml) was treated dropwise with a solution of 1-benzyl-1,6-dihydro-5-methoxy-3-[2H]pyridone (16.3 g, 75 mM) in THF (75 ml) and stirred 1 hour. The reaction mixture was poured onto cold 2 N hydrochloric acid (150 ml) and stirred 30 min. Removal of the resulting precipitate by filtration, followed by air-drying and recrystallisation from ethanol gave the title compound as the hydrochloride hydrate (14.7 g) m.p. 143°–5°.

Analysis: Found: C, 61.3; H, 5.1; N, 3.5%, $C_{18}H_{16}ClNO.HCl.H_2J$ requires C, 61.3; H, 5.4; N, 4.0%.

EXAMPLE 15

1-Benzyl-1,6-dihydro-5-(p-chlorophenyl)-3[2H]-pyridone

A solution of p-chlorophenyl magnesium bromide (0.17 M) in ether (100 ml) was treated with a solution of 1-benzyl-1,6-dihydro-5-methoxy-3-[2H]pyridone (32.5 g, 0.25 M) in THF (150 ml). The reaction was stirred 1 hour, poured onto cold 2 N hydrochloric acid (250 ml) and stirred 30 min. Removal of the resulting precipitate by filtration, followed by air-drying and recrystallisation from methanol gave the title compound as the hydrochloride hydrate (24.1 g) m.p. 166°–8°.

Analysis: Found: C, 61.7; H, 5.0; N, 3.7%, $C_{18}H_{16}ClNO.HCl.H_2O$ requires C, 61.3; H, 5.4; N, 4.0%.

EXAMPLE 16

5-Methoxy-1-methyl-1,6-dihydro-3[2H]-pyridone (a) To a suspension of potassium hydride (90 g of 24.5% dispersion in oil) in ether (2.5 l.) under nitrogen was added t-butanol (2.5 ml) followed by methyl N-acetonyl-N-methylglycinate (79.6 g) in ether (500 ml). The reaction mixture was stirred for 1 hour and resulting precipitate removed by filtration, washed with ether and dried in vacuo to give the potassium salt of 1,6-dihydro-5-hydroxy-1-methyl-3[2H]pyridone (70 g).

(b) By a procedure analogous to that of Example 1(b), the potassium salt of 1,6-dihydro-5-hydroxy-1-methyl-3-[2H]pyridone is converted to 5-methoxy-1-methyl-1,6-dihydro-3[2H]pyridone, m.p. 71°–72°.

EXAMPLE 17

1,6-Dihydro-1-methyl-5-(3,4-dimethoxyphenyl)-3[2H]-pyridone

A solution of 3,4-dimethoxyphenyl magnesium bromide (0.23 M) in THF (150 ml) was treated with a solution of 5-methoxy-1-methyl-1,6-dihydro-3[2H]pyridone (28.2 g, 0.2 M) at such a rate as to maintain gentle reflux. After 1 hour the reaction mixture was poured on to methanol (500 ml) and then treated with 12 N hydrochloric acid (50 ml). The resulting precipitate was removed by filtration and air-dried to give the title compound as the hydrochloride (32.2 g) m.p. 248°.

EXAMPLE 18

1,6-Dihydro-1-methyl-5-phenyl-3[2H]-pyridone

A solution of phenyl magnesium bromide (0.31 M) in ether (200 ml) was treated with a solution of 5-methoxy-1-methyl-1,6-dihydro-3[2H]pyridone (40 g, 0.28 M) in benzene (200 ml) at such a rate as to maintain gentle reflux. After completion of the addition, a solution of acetic acid (18 ml) in water (200 ml) was added. The aqueous layer was extracted with ether (2×250 ml), the combined organic layers washed with brine, dried (MgSO$_4$) and treated with an excess of ethereal hydrogen chloride. The resulting precipitate was removed by filtration and recrystallised from methanol to give the title compound as the hydrochloride (19 g), m.p. 175°–177°.

EXAMPLE 19

1,6-Dihydro-5-(4-methylphenyl)-1-methyl-3[2H]-pyridone

A solution of p-tolyl magnesium bromide (0.23 M) in ether (150 ml) was treated with a solution of 5-methoxy-1-methyl-1,6-dihydro-3[2H]pyridone (28.2 g, 0.2 M) in THF (200 ml) at such a rate as to maintain a gentle reflux. After 1 hour the reaction mixture was poured on to methanol (500 ml) and treated with 12 N hydrochloric acid (50 ml). Removal of the resulting crystals by filtration followed by air-drying gave the title compound (21 g) as the hydrochloride five quarters hydrate.

Analysis: Found: C, 60.2; H, 6.75; N, 5.4; $C_{13}H_{15}NO.HCl.5/4 H_2O$ requires: C, 60.0; H, 7.2; N, 5.4%.

EXAMPLE 20

5-Hydroxy-1-methyl-3-(4-methylphenyl)-1,2,5,6-tetrahydropyridine

A solution of 1,6-dihydro-5-(4-methylphenyl)-1-methyl-3[2H]pyridone hydrochloride (18 g) in 50% aqueous ethanol (500 ml) was treated with sodium bicarbonate (6.4 g) followed by sodium borohydride (4 g) in portions. After 2 hours, the solvent was removed under reduced pressure and the residue extracted with ether (2×250 ml). Drying (MgSO$_4$) followed by removal of the solvent under vacuum gave an oil which crystallised and was recrystallised from pentane to give the title compound (9 g) m.p. 67°–69°.

Analysis Found: C, 77.1; H, 8.4; N, 6.7%. $C_{13}H_{17}NO$ requires: C, 76.8; H, 8.4; N, 6.9%.

EXAMPLE 21 cis-3-Hydroxy-1-methyl-5-(4-methylphenyl)piperidine

A solution of 5-hydroxy-1-methyl-3-(4-methylphenyl)-1,2,5,6-tetrahydropyridine (5.1 g, 25 mM) in methanol (200 ml) was hydrogenated in a Parr apparatus at 50 psi (about 3.51×10$^4$ kg/sq.m.) and room temperature over 10% palladium-on-charcoal (1 g). After the theoretical uptake of hydrogen had occurred (about 3 hours) the catalyst was removed by filtration and the solvent removed under vacuum. Recrystallisation from cyclohexane gave the title compound (4 g). A portion was converted to the hydrochloride and recrystallized from methanol/ether to give the title compound hydrochloride, m.p. 218°-9°.

Analysis: Found: C, 64.4; H, 8.75; N, 6.0% $C_{13}H_{19}NO \cdot HCl$ requires: C, 64.6; H, 8.3; N, 5.8%.

We claim:

1. A process for preparing a dihydropyridine derivative of formula

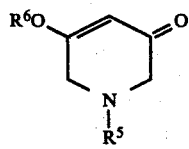

where $R^5$ is lower alkyl or aryl(lower)alkyl and $R^6$ is lower alkyl which comprises (a) cyclising an ester of formula (IV)

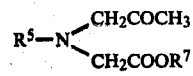

where $R^5$ is as defined above and $R^7$ is alkyl, aryl or aralkyl, by reaction with sodium or potassium hydride in an inert solvent;

(b) isolating the resulting sodium or potassium salt of formula

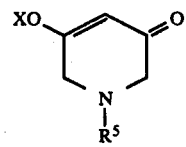

where $R^5$ is as defined above and X is sodium or potassium, and (c) reacting sodium or potassium salt of formula (III) with an alkylating agent in a polar aprotic solvent.

* * * * *